United States Patent [19]

Waters

[11] Patent Number: 5,744,654
[45] Date of Patent: Apr. 28, 1998

[54] RECOVERY OF PARA-ETHYLPHENOL

[75] Inventor: John A. Waters, Houston, Tex.

[73] Assignee: Merichem Company, Houston, Tex.

[21] Appl. No.: 663,649

[22] Filed: Jun. 14, 1996

[51] Int. Cl.$^6$ .................................... C07C 39/06
[52] U.S. Cl. ...................................... 568/750
[58] Field of Search .................. 568/750, 751, 568/568, 566

[56] References Cited

U.S. PATENT DOCUMENTS

| 2,490,670 | 12/1949 | Cislak et al. | 260/621 |
| 2,882,244 | 4/1959 | Milton | 252/455 |
| 3,014,078 | 12/1961 | Fleck et al. | 260/261 |
| 3,855,333 | 12/1974 | Neuzil | 260/674 |
| 3,917,734 | 11/1975 | deRosset | 260/674 |
| 3,969,422 | 7/1976 | Neuzil et al. | 260/621 |
| 4,124,770 | 11/1978 | Miyake et al. | 568/758 |
| 4,356,331 | 10/1982 | Inuoe et al. | 568/758 |
| 4,386,225 | 5/1983 | Neuzil | 568/758 |
| 4,847,435 | 7/1989 | Kase et al. | 568/750 |
| 5,149,887 | 9/1992 | Zinnen | 568/751 |

FOREIGN PATENT DOCUMENTS 2291056  1/1996  United Kingdom ............ C07C 39/06

OTHER PUBLICATIONS

CA 126 : 74571 Suzuki Myo Abst 1996 Nov. 5—"Separation of Ethylphenol Isomers by Using Zeolites as Adsorb".
CA 126 : 31156 Murimoto 1996 Oct 15 Abst. Sep of Alkylphenol Isomers by Using Zeolites.
CA 125 : 328283 Sep. 24, 1996 Abst "Separat of Alkylphenol Isomers".

Primary Examiner—C. Warren Ivy
Assistant Examiner—Jean F. Vollano
Attorney, Agent, or Firm—Jenkeus & Gilchrist P.C.

[57] ABSTRACT

A process for separating and recovering para-ethylphenol from methyl-ethylphenol and other alkyl phenols is described using an X zeolite adsorbent having ion exchangeable sites exchanged with barium ions, potassium ions or a mixture of barium and potassium ions. Selective adsorption of para-ethylphenol occurs possibly for recovery of the para-ethylphenol.

6 Claims, 4 Drawing Sheets

RECOVERY OF PARA-ETHYLPHENOL

BACKGROUND OF THE INVENTION

This invention relates to a process of separating p-ethylphenol from m-ethylphenol, even from mixtures containing xylenols using a type X zeolite adsorbent.

The art is replete with discussions of the separation of alkyl phenols using zeolite adsorbents. These type X and type Y zeolites are well known and most of the work described by the art has involved adsorption separations of the cresol isomers and xylenols from other alkyl phenols, including the ethylphenol isomers. There are also described adsorbent/desorbent systems for recovering one or more of the cresol isomers from such mixtures. For example, adsorptive processes are described in, for example, U.S. Pat. Nos. 3,014,078; 3,969,422; 4,356,311; 4,124,770; 4,386,225; and 5,149,887 as representative patents describing not only such processes but the zeolite adsorbents themselves useful in such processes.

Even in the presence of such extensive studies of the adsorptive separation processes for these alkyl phenols the separation of m-ethylphenol and p-ethylphenol as described in U.S. Pat. No. 4,847,435 using zeolite with a constraint index greater than 20 required that the p-ethylphenol first be selectively adsorbed from the mixture on certain aluminosilicate catalysts and then be dealkylated at high temperatures to yield ethylene and phenol in order to recover a highly pure m-ethylphenol. Thus, the para isomer is sacrificed. Also, U.S. Pat. No. 2,490,670 described the separation of p-ethylphenol and m-ethylphenol by reacting them with an inorganic base and then separating them through crystallization and filtration. Neither method is convenient for recovery of p-ethylphenol.

A separation of p- and m-cresol isomers from a mixture containing them along with at least one other alkyl phenol, including the ethylphenols, is described in U.S. Pat. No. 5,149,887 using an X zeolite exchanged at exchangeable cationic sites with barium and potassium ions. A rigorous description of the zeolite is present in this patent. But, while the zeolite is applicable to the practice of the present invention, the separation process described herein went undetected.

A printed application, GB 2291056A describes the use of a K—Y type zeolite adsorbent in a adsorption-desorption process for the separation of p-ethylphenol from m-ethylphenol. However, it is observed that Y-type zeolites cause unacceptable side reaction byproducts causing arduous work-up steps in a commercial process. This formation of byproducts can lead to pore blockage, fouling of the sieves and premature shut-down of the process. This gets worse at higher temperatures.

Accordingly, it is an object of this invention to provide a process for the separation and recovery of p-ethylphenol from other ethylphenol isomers and the commonly present xylenol isomers.

It is a further object of this invention to separate p-ethylphenol from m-ethylphenol appearing in binary mixtures.

It is a still further object of this invention to provide such separation with high selectivity towards the p-ethylphenol without the formation of unacceptable byproduct contamination of the p-ethylphenol.

SUMMARY OF THE INVENTION

The present invention is a process for separating and recovering p-ethylphenol from alkyl phenol mixtures, including the para and meta isomers of ethylphenol or the isomers of ethylphenol in the presence of other alkyl phenols, particularly xylenols and/or cresols. The process is practiced by contacting the feed mixture with an adsorbent comprising an X type zeolite, exchanged at ion exchangeable sites with barium ions, potassium ions or a mixture of barium and potassium ions. This exchange makes the material particularly selective for adsorbing p-ethylphenol in relation to m-ethylphenol. Thereafter, the p-ethylphenol is recovered by contacting the adsorbent with a desorbent at liquid phase desorption conditions. The desorbent may preferably be an aliphatic alcohol or ketone. In the practice of this invention, the prepared desorbent is pentanol. The p-ethylphenol is separated from the desorbent by distillation or flashing and the desorbent may then recycled. In a commercial process the above sequence would be carried out several times in "zones," generally in a "simulated moving bed" apparatus as described in patents above and well known in the art.

Other embodiments of the present invention encompass the details about feed mixtures adsorbent and desorbent materials, flow schemes and operating conditions, all of which are either disclosed in the discussion or are within the experience of the person of ordinary skill in the art.

DESCRIPTION OF THE INVENTION

Figure 1:
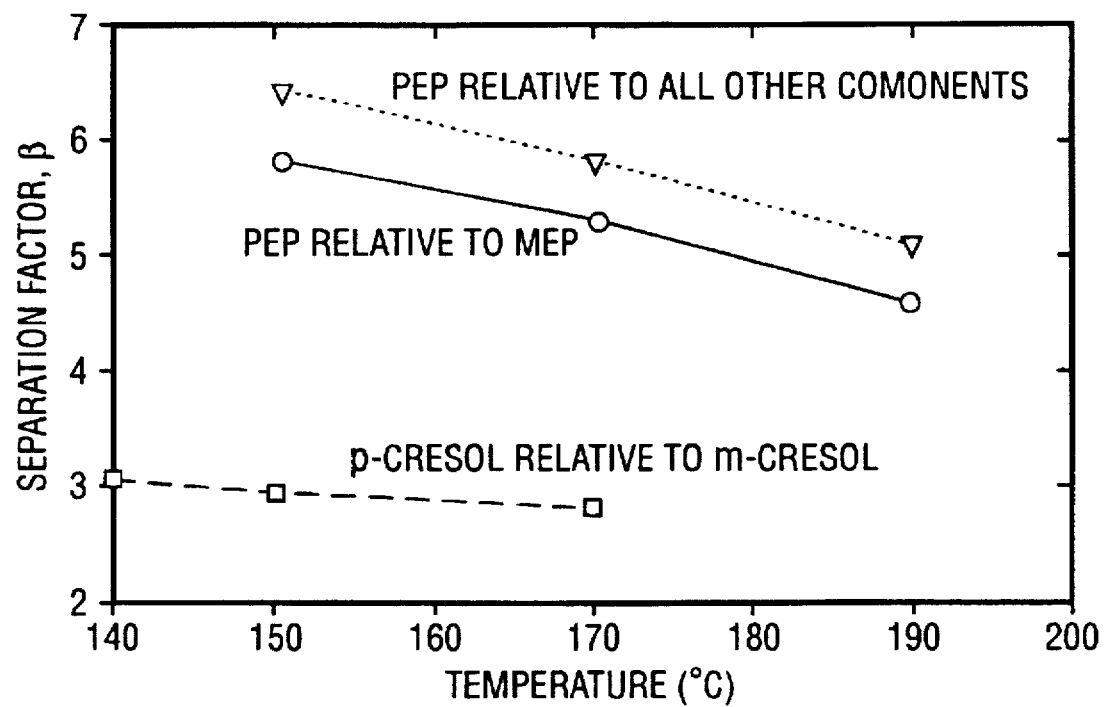
FIG. 1 shows separation factors, $\beta$, for the separation of p-cresol and m-cresol in comparison with higher $\beta$ for the separation of p-ethylphenol from m-ethylphenol.

The adsorbents to be used in the process of this invention are generally characterized as type X zeolites exchanged at exchangeable cationic sites with barium and or potassium ions. These zeolites are more particularly described in U.S. Pat. Nos. 2,882,244; 3,969,422; 4,356,331; and 5,149,887, which are incorporated herein by reference for all purposes. The term "type X structured zeolites" include those types mentioned in the above patents. The cation exchange activity with respect to the zeolite is described in U.S. Pat. Nos. 5,149,887 and 3,969,422, incorporated herein by reference for all purposes. X-type zeolite belong to a class of aluminum silicates known as faujasites. The basic composition of a sodium-X zeolite is $Na_{86} \cdot (SiO_2)_{106} \cdot 264 \, H_2O$. The sodium ions can, to a large extent, be exchanged for barium and/or potassium ions, which process makes the material particularly selective for adsorbing p-ethylphenol in relation to m-ethylphenol for practicing the process of this invention. The crystalline zeolites, which are generally obtained as microcrystals, are generally formed into large particles (pellets) for commercial application. This very often necessitates the use of a binder material, which is prepared even if not necessary.

Typically, adsorbents used in separative processes contain the crystalline material dispersed in an amorphous inorganic matrix, or binder, having channels and cavities therein which enable liquid access to the crystalline material. Adsorbents which have shown good applicability in the practice of this invention to separate p-ethylphenol from m-ethylphenol are those which also are useful for separating p-cresol from m-cresol where the p-isomer is the adsorbed species. Surprisingly, however, where the separation factor for p-cresol relative to m-cresol is around 3, the separation factor, $\beta$, for p-ethylphenol relative to m-ethylphenol has been observed to be from 5 to 6 for comparable temperatures of operation with the same zeolite adsorbent. The separation factor, $\beta$, is determined by the chromatographic separation carried out in the so-called "pulse test" which is well known and widely described.

Even though the process can operate either in the liquid or vapor phase to achieve attractive separations, the liquid phase operation is preferred, in view of the lower temperature requirements, and because the higher yields of the p-ethylphenol can be obtained in the liquid phase operation. Adsorption conditions will include a temperature range of from about 20° to about 200° C. and sufficient pressure to maintain the system in the liquid phase. The pressure range would be from about atmospheric to about 500 psig (about 35 kg/cm$^2$), which would also be the range of temperatures and pressures for the desorption step of the process.

The feedstock for the separation and recovery of p-ethylphenol is normally a distillation fraction resulting from a process for the separation of xylenols, and is accompanied by many other alkyl phenols in what would normally be part of a feedstream for the recovery of cresols. As originally constituted, xylenois, cresols and the alkylphenols, including the isomers of ethylphenol, are present in the feed. The cresols herein contemplated encompass all isomers, namely o-cresol, m-cresol and p-cresol. Likewise, xylenols include all isomers as represented by the position of methyl groups, i.e. (2,6), (2,3), (2,4), (2,5), (3,4) and (3,5). Typical examples of the feed mixture for which the present invention can suitably be applied are a mixture of xylenol isomers and trimethylphenol isomers, in addition to the p-ethyl- and m-ethylphenols. The mixture may further contain other substances such as phenol; other alkylphenols, e.g. cresols, tert-butyl cresol isomers, di-tert-butyl cresol isomers, α-naphthol, β-naphthol, carvacrol, thymol, phenylphenol, benzylphenol, pyrocatechin, pentadecyl, catechol, guaiacol, eugenol, iso-eugenol; and halogenated phenols. The composition of the mixture is not limited but may vary widely and presence of third components is also admissible.

The overall feed, the gross stream from coal tar, for example, would normally undergo preprocessing which would result in a separation of the cresols, ortho-ethylphenol and 2,6-xylenol, leaving a mixture of other materials. A typical analysis is shown in Table 1 of such a mixture which may be used as feed for the practice of the process of this invention.

TABLE 1

| COMPONENT | MIDDLE DISTILLATE STREAM |
|---|---|
| Phenol | .04 |
| o-Cresol | .08 |
| 2,6 Xylenol | tr |
| M,P Cresol | .21 |
| OEP | .31 |
| 2,4/2,5 Xylenols | 3.81 |
| 2,3 Xylenols | 13.16 |
| PEP | 25.00 |
| MEP | 32.15 |
| 2,4,6 TMP | 1.40 |
| 3,5 Xyl | 18.51 |
| 3,4 Xyl | 2.54 |
| Higher Alkylphenols | 2.79 |

The above-identified feedstock may be enhanced by distillation such that p-ethylphenol may constitute about 35 % by wt. of the mixture remaining for use in the separation process.

The procedures and descriptions of the adsorption/desorption process are well known to those skilled in the art as is the selection of the desorbent used which may be polar compound such as alcohols, amides, amines, ethers, esters, nitrites, nitro-compounds, halogenated hydrocarbons and sulfur compounds. The desorbents should be easily separated from the p-ethylphenol. Preferred embodiments of the practice of this invention involve the use of ketones and alcohols or mixtures thereof which boil at least about 5° C. from the boiling point of the p-ethylphenol. This makes separation simple and complete. Especially preferred are the use of $C_4$ to $C_6$ alcohols as desorbents.

In the preferred isothermal, isobaric, liquid-phase operation of the process of the invention, desorbent materials comprising aliphatic alcohols ($C_4$ to $C_6$), selected to differ in boiling point by at least 5° C. from the boiling range of the feedstock so the desorbent may be easily recovered for reuse, will result in selectivity for the coextracted product when used with the above discussed adsorbent.

Although both liquid and vapor phase operations can be used in many adsorptive separation processes, liquid-phase operation is preferred for this process because of the lower temperature requirements, and because of the higher yields of extract product that can be obtained with liquid phase operation over those obtained with vapor-phase operation. Adsorption conditions will include a temperature range from about 20° to about 200° C., probably from about 140° C. to about 200° C., and a pressure sufficient to maintain a liquid phase, ranging from about atmospheric to about 500 psig (about 35 kg/cm$^2$). The pressure may, on occasion, go up to about 40 kg/cm$^2$. Desorption conditions will include the same range of temperatures and pressures as used for adsorption conditions. Preferably, the temperatures should be kept as low as possible within the operable parameters of the system in order to preserve adsorbent life and limit the formation of by products.

At least a portion of the extract stream, and preferably at least a portion of the raffinate stream, from the separation process, are passed to separation means, typically fractionators or evaporators, where at least a portion of the desorbent material is separated to produce a co-extract product and a raffinate product, respectively. The raffinate will contain the less strongly adsorbed components of the feed, e.g., m-ethylphenols and xylenols in this process.

A dynamic test for determining the sufficiency of the separation, called a pulse test, well known to those skilled in the art is described, for example, in U.S. Pat. Nos. 3,969,422; 5,149,887; and 3,917,734. The results of such tests are normally determined by chromatographic analysis from which the relative selectivity, or separation factor, $\beta$, is determined. This factor is defined as the ratio of the two components in the adsorbed phase divided by the ratio of the same two components in the unadsorbed phase at equilibrium conditions. If the selectivity of the two components is equal, i.e., $\beta=1$, there is no preferential adsorption of one component with respect to the other. It takes a $\beta$ of about 1.6 or greater to be considered sufficient separation factor to accomplish a commercially satisfactory recovery. Note on FIG. 1 that the $\beta$ for p-cresol relative to m-cresol is relatively constant at about 3 from the temperatures of 140° C. to 170° C., while $\beta$ of p-ethylphenol relative to m-ethylphenol when separated from a binary system at a temperature of from 150° C. to 170° C. runs between 5.5 and 6 using the same adsorbent X-type zeolite. When the p-ethylphenol is compared with all other components in a middle distillate cut, the $\beta$ runs from 6 to about 6.5. These results are pleasantly surprising since the separation is accomplished without significant formation of unwanted byproducts that are usually found when highly active adsorbents are used, such as, for example, Y-type zeolites.

The foregoing described invention will be better specifically illustrated by the following examples which are offered for purposes illustration rather than limitation.

EXAMPLE 1

Static Selectivity Measurements at 23° C. and at 165° C.

A sample of 10 g of a barium, potassium exchanged sodium X zeolite was immersed in 20 g of a mixture of xylenols and ethylphenols of composition: 2,4 xylenol, 1.88%; 2,5 xylenol, 2.53%; 2,3 xylenol, 14.7%; p-ethylphenol, 14.97%; m-ethylphenol, 38.25%; 3,5 xylenol, 20.27%; 3,4 xylenol, 3.16%; alkylphenols 1.5%. The ratio of m-ethylphenol/p-ethylphenol was 2.55 in the original mixture. It increased to 2.67 in the supernatant liquid, indicating preferential adsorption by the sieve of p-ethylphenol. When this test was repeated at 165° C. the supernatant liquid contained m-ethylphenol and p-ethylphenol in a ratio of 2.63—confirming the results obtained at 23° C. and indicating a promising separation. This example can be repeated with any candidate zeolite for use in the process of this invention.

EXAMPLE 2

Pulse Test Values using a Ba—K—X—Zeolite and Ethylphenols in Xylenols

The dynamic selectivity separation factor $\beta$ was determined using the feed as set forth in Example 1 in a pulse test experiment using pentanol as the desorbent at 177° C. The adsorbent was commercially available from UOP, Inc. (DesPlaines, Ill.) under the name of ADS-8 and was made according to U.S. Pat. No. 3,855,333. Values for the separation factors for the various relevant isomers were:

$$\beta \frac{\text{p-ethylphenol}}{\text{m-ethylphenol}} = 6.38$$

$$\beta \frac{\text{p-ethylphenol}}{2,3\text{-xylenol}} = 11.33$$

$$\beta \frac{\text{p-ethylphenol}}{3,5\text{-xylenol}} = 17.00$$

$$\beta \frac{\text{p-ethylphenol}}{\text{pentanol}} = 1.93$$

The separation of p-ethylphenol from xylenols and m-ethylphenols was dramatic while nearly the same adsorbance existed as the desorbent, pentanol.

EXAMPLE 3

As a comparison test for the separation efficiency of p-ethylphenol (PEP) from m-ethylphenol (MEP), a pulse test was run on a test liquor of the following composition:

| Isomer | Content (%) |
|---|---|
| 2,4-xylenol | 0.254 |
| 2,5-xylenol | 0.310 |
| 2,4,6-trimethylphenol | 0.605 |
| 2,5-xylenol | 1.460 |
| p-ethylphenol | 4.740 |
| m-ethylphenol | 15.270 |
| 3,5-xylenol | 42.29 |
| 3,4-xylenol | 19.84 |
| Alk #1 | 14.70 |

Two commercially available zeolite adsorbents were used in two systems to demonstrate the ease of separation. The ADS-8(X-type)/Pentanol System was run at 177° C. and the T-95(Y-type) zeolite with butanol/diethyl ketone desorbent was run at 130° C. The results of the pulse test are shown on Table II:

TABLE II

RECENT PULSE TEST DATA

| ZEOLITE AND DESORBENT | TEMP. (°C.) | $\beta$ PEP/MEP | $\beta$ PEP/2,3 | $\beta$ PEP/3,5 | $\beta$PEP/ Desorbent | $\beta$p-/m- Cresol |
|---|---|---|---|---|---|---|
| Toray T-95/BuOH/DEK[1] | 130 | 5.86 | 7.82 | 6.79 | 3.09 | 3.09 |
| ADS-8/Pentanol[2] | 177 | 6.38 | 11.33 | 17.00 | 1.93 | 2.35 |

[1]U.S. Pat. 4,356,331
[2]U.S. Pat. 3,855,333

As is shown on Table II, the $\beta$, or selectivity, for the p-ethylphenol (PEP) for both systems is greater than about 5. However, the system with the Y-type zeolite created troublesome byproducts while a high grade of p-ethylphenol was recovered from the relatively complex mixture using the X-type zeolite. The B separation factor is dramatically greater than the separation factor for the cresol isomer separation in both cases. Since the β of the PEP/desorbent couple is closer to unity (one), it shows its applicability to the separation process, particularly with the second zeolite in the Table.

EXAMPLE 4

Using a commercially available X zeolite having a faujasite structure sold under the designation ADS-38 by UOP (Des Plaines, Ill.) a series of experiments were run using a pulse test incorporating three nominal 0.5-inch (inside diameter) liquid chromatography columns in series. About 49.2 g of ADS-38 zeolite was placed into the columns. The columns were placed in an oven and the temperature adjusted to test temperature. The initial water content of the zeolite was 1.6% (by KF titration) which corresponds to about 5.3% water by the loss on ignition test at 900° C. The desorbent was pumped through the system with pulse injections of the feed. The concentration of the components of the separation feed in the pulse were about 3 wt. %. Feed components were injected alone or as a binary MEP/PEP 50% mixture, or as the middle distillate material as defined below. Feedrate was about 1.5 cc/per minute, or 1.21 g per minute, with a variation of ±0.01 g per minute. A pentanol solvent, the desorbent used in the test, was used as the base carrier material for the tests. The pentanol water level was about 50 ppm going into the adsorbent. The distillate feed had a composition of: 0.3 wt % 2,4-/2,5-xylenol, 0.8 wt % 2,4,6-TMP, 8.2 wt % 2,3-xylenol, 28.9 wt % PEP, 55.5 wt % MEP, and 6.3 wt % 3,5-xylenol(+). The PEP/MEP weight ratio in the feed was 0.52.

Figure 3A:
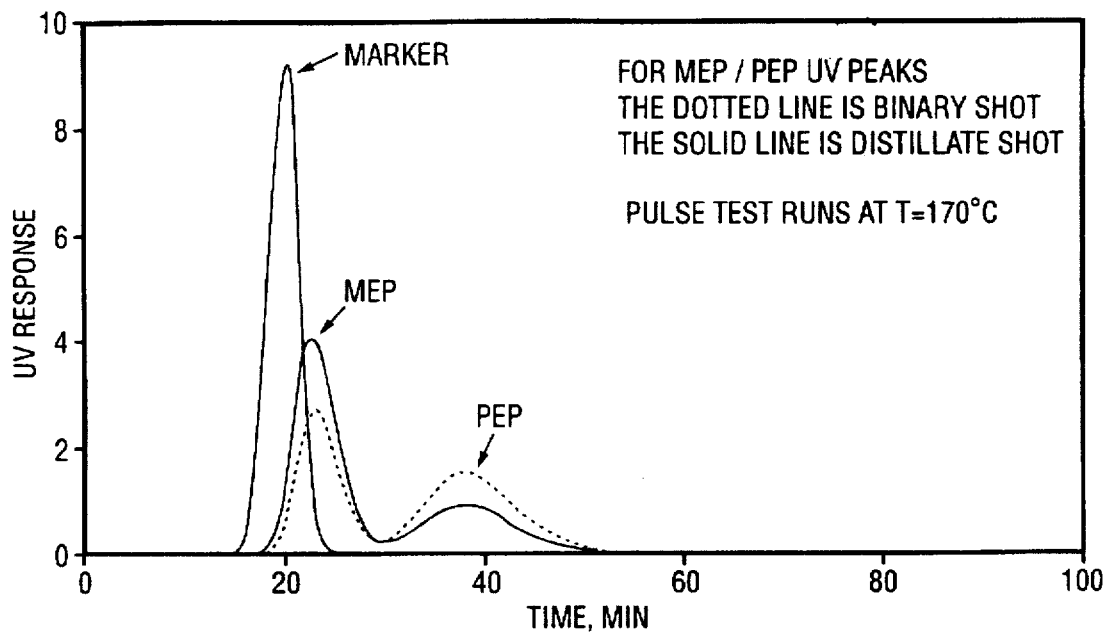
FIG. 3A shows the chromatographic UV peaks resulting from the pulse test run at 170° C.
Figure 3B:
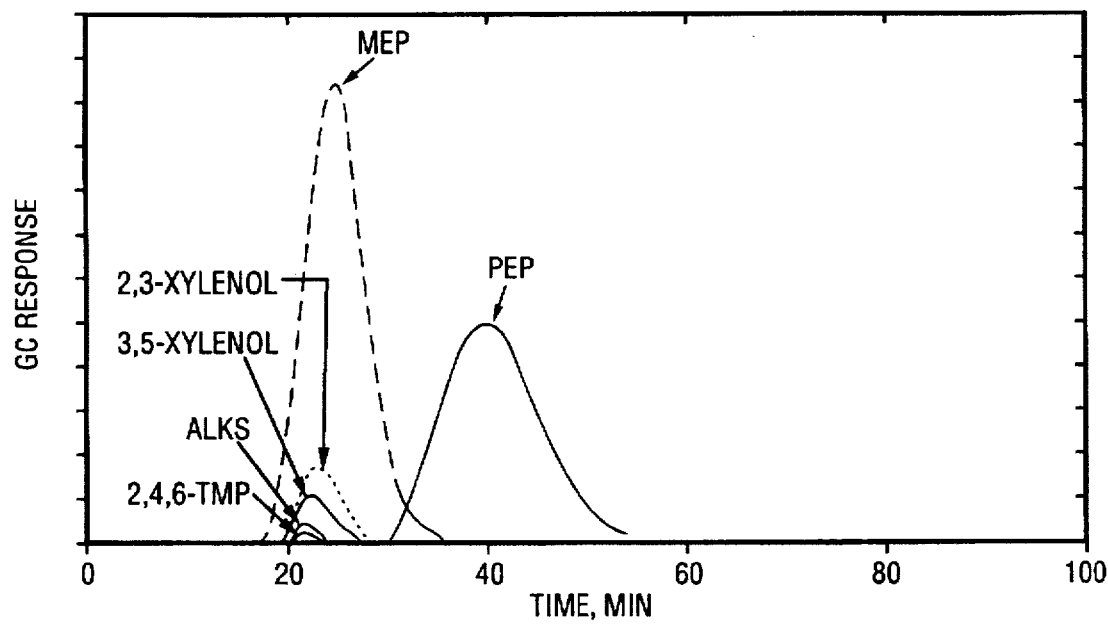
FIG. 3B shows the gas chromatographic responses recorded from pulse tests run at 170° C.
Figure 4A:
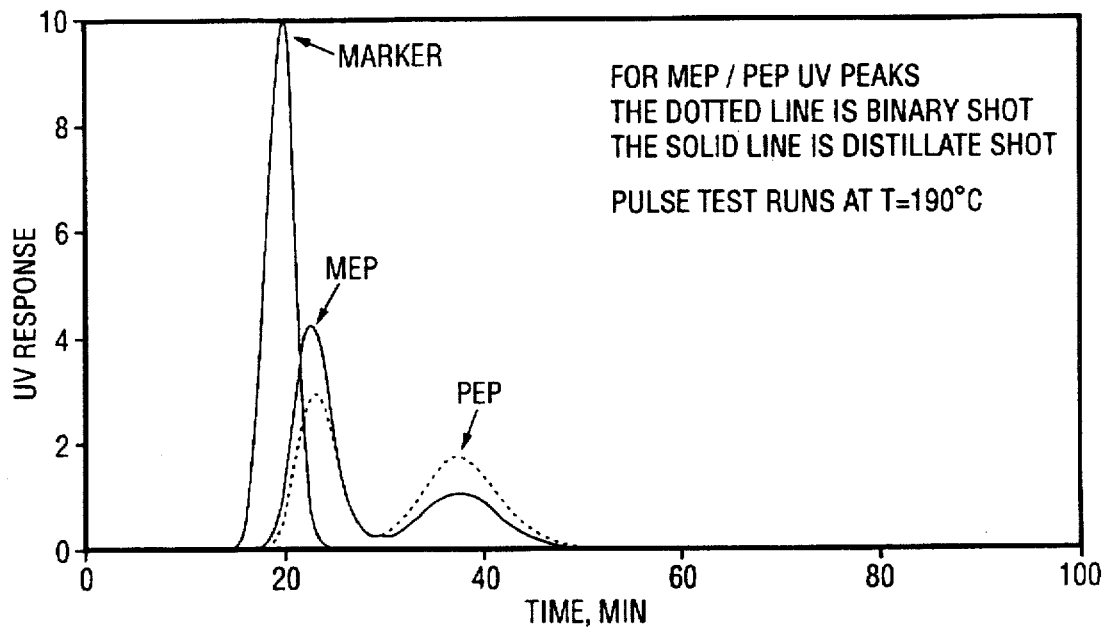
FIG. 4A shows the chromatographic UV peaks resulting from the pulse test run at 190° C.
Figure 4B:
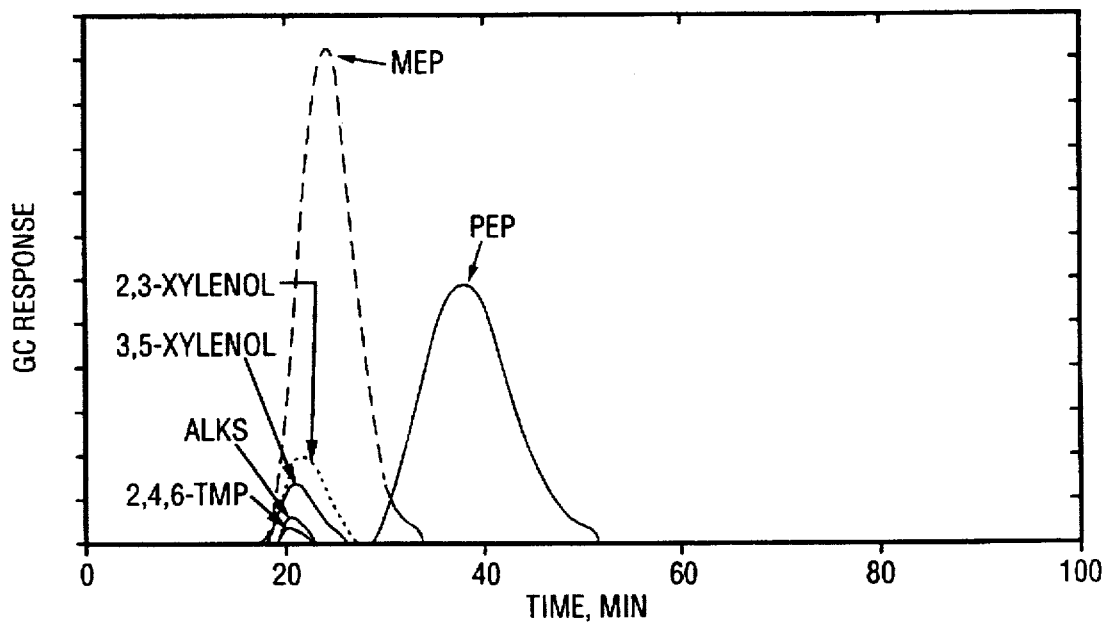
FIG. 4B shows the gas chromatographic responses recorded from pulse tests run at 190° C.

All pulse tests run were analyzed using an ultraviolet detector (UV) on the product. The maximum adsorbance was 0.627 at 280 nM with the 3% MEP pulse. In some pulse test using distillate, the distillate shots were analyzed by taking discrete 10 second samples and analyzing them using gas chromatography (GC). Analyses of pulse tests that used both UV and GC analyses are shown in FIGS. 2 through 4. The main components in the feed, not MEP or PEP, eluted with the MEP and well before the PEP as illustrated in FIGS. 2-4.

Figure 2A:
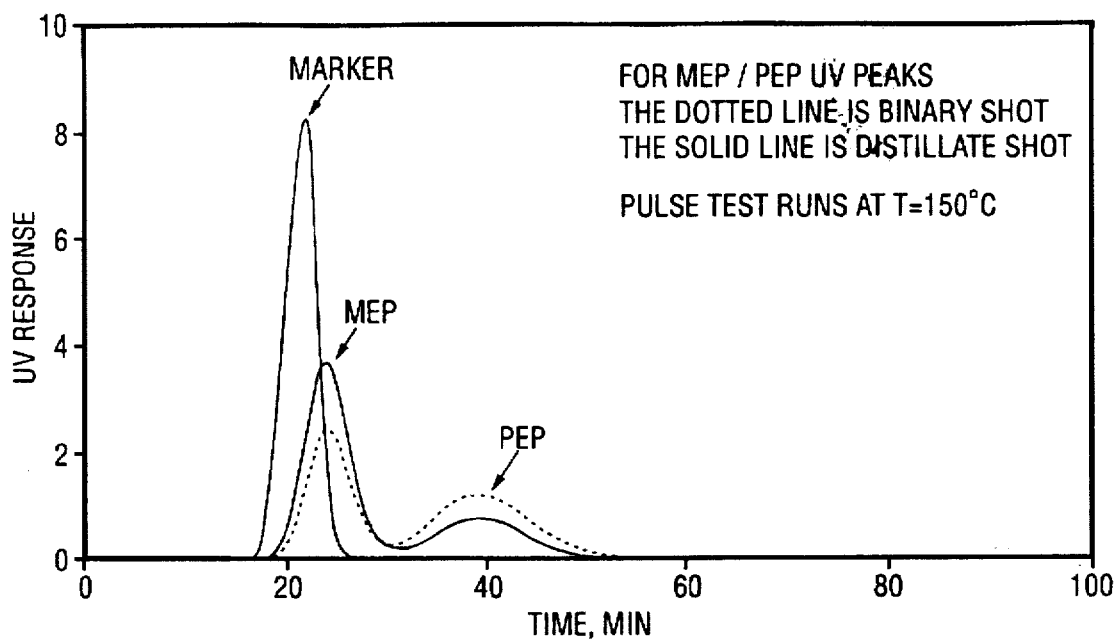
FIG. 2A shows the chromatographic UV peaks resulting from the pulse test run at 150° C. with the dotted line showing peaks taken when the feed is a binary mixture of isomers and the solid line shows the results where the feed is a distillate containing the isomer.
Figure 2B:
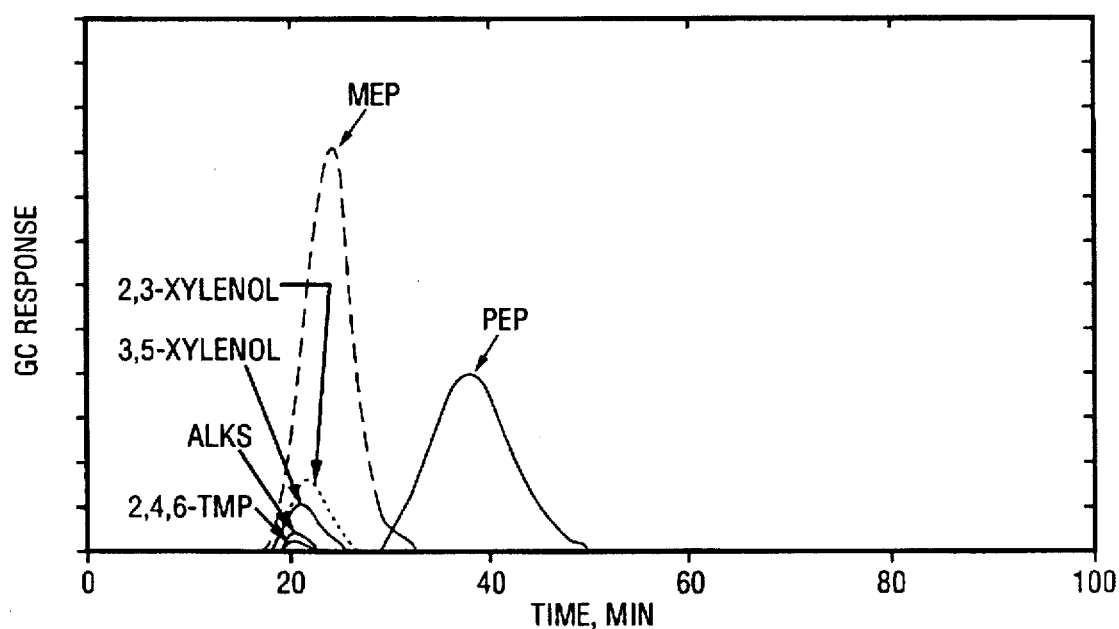
FIG. 2B shows the gas chromatographic responses recorded from pulse tests run at 150° C.

A series of determinations were made and the data that were collected were plotted FIG. 1. The FIGS. 2A and 2B show representative results of pulse tests run at 150° C. FIGS. 3A and 3B show the same data of pulse tests run at 170° C., and FIGS. 5A and 5B show the test data run at 190° C. It is noted from all the foregoing figures that the degree of separation of PEP and MEP is very dramatic. In the graphical representations of the pulse tests data, the difference in the peaks of the PEP and marker divided by the difference of the MEP and the marker give the determination of the separation factor, β.

Having described the invention above, one of ordinary skill in the art would adopt many variations in ingredients and process parameters without departing from the scope of the foregoing described invention or the appended claims.

What is claimed:

1. A process for the separation and recovery of p-ethylphenol from a complex mixture comprising p-ethylphenol, m-ethylphenol, and other alkylphenols without significant formation of unwanted byproducts which comprises the steps of contacting the mixture at adsorption conditions with a type X-zeolite exchanged at ion exchangeable sites with barium ions, potassium ions or a mixture of barium and potassium ions to selectively adsorb p-ethylphenol, contacting said adsorbent and adsorbed p-ethylphenol with a desorbent material having a boiling point at least about 5° C. different from the boiling point of p-ethylphenol, at desorption conditions sufficient to maintain a liquid phase, whereby p-ethylphenol is recovered at a separation factor of about 4.5 or greater relative to the m-ethylphenol present in the feed and to all other alkylphenols present in the feed.

2. The process of claim 1 wherein both the adsorption and desorption steps occur at a temperature of from about 140° C. to about 200° C.

3. The process of claim 2 wherein the desorbent is a $C_4$ to $C_6$ alcohol.

4. The process of claim 3 wherein the desorbent is n-pentanol.

5. The process of claim 1 wherein the p-ethylphenol is recovered from the desorbent material.

6. A process for separating and recovering p-ethylphenol from a mixture comprising p-ethylphenol and m-ethylphenol which comprises the steps of contacting the mixture at adsorption conditions with a type X-zeolite exchanged at ion exchangeable sites with barium ions, potassium ions or a mixture of barium and potassium ions to selectively adsorb p-ethylphenol, contacting said adsorbent containing p-ethylphenol with an $C_4$ to $C_6$ aliphatic alcohol desorbent at desorption temperature and pressure conditions to maintain a liquid phase, whereby p-ethylphenol is recovered at a separation factor of about 4.5 or greater relative to the m-ethylphenol.

* * * * *